United States Patent [19]

Deguchi et al.

[11] 4,369,134

[45] Jan. 18, 1983

[54] CREAMY CLEANSING COMPOSITIONS

[75] Inventors: Katsuhiko Deguchi, Sakura; Masatoshi Arisawa, Matsudo; Atsuo Ishida, Chiba; Katsuaki Ooshima, Tokyo, all of Japan

[73] Assignee: Kao Soap Co., Ltd., Tokyo, Japan

[21] Appl. No.: 230,698

[22] Filed: Feb. 2, 1981

[30] Foreign Application Priority Data

Feb. 5, 1980 [JP] Japan .................. 55-12623
Apr. 3, 1980 [JP] Japan .................. 55-43710

[51] Int. Cl.³ ................... C11D 1/86; C11D 3/075
[52] U.S. Cl. ................... 252/526; 252/174.14; 252/174.16; 252/528; 252/529; 252/545; 252/547; 252/548; 252/DIG. 5; 252/DIG. 13; 252/DIG. 17
[58] Field of Search ............ 252/174.16, 545, 547, 252/DIG. 5, DIG. 14, DIG. 17, 526, 528, 174.14

[56] References Cited

U.S. PATENT DOCUMENTS

| 3,862,045 | 1/1975 | Sato et al. ................. 252/8.75 |
| 4,132,679 | 1/1979 | Tsutsumi et al. ............ 252/545 |
| 4,139,485 | 2/1979 | Imokawa et al. ............ 252/135 |
| 4,259,204 | 3/1981 | Homma ..................... 252/174.16 |

FOREIGN PATENT DOCUMENTS

| 2455651 | 6/1975 | Fed. Rep. of Germany . |
| 2449354 | 4/1976 | Fed. Rep. of Germany . |
| 2389671 | 3/1977 | France . |
| 1321579 | 6/1973 | United Kingdom . |
| 1495253 | 12/1977 | United Kingdom . |
| 2028133 | 5/1980 | United Kingdom . |
| 1578641 | 11/1980 | United Kingdom . |

OTHER PUBLICATIONS

Chemical Abstracts, vol. 93, No. 6, Aug. 1980, p. 449, column 1, No. 53769j & JP-A 80 04347 (Lion Fat and Oil Co., Ltd.), 12-01-80.
Chemical Abstracts, vol. 88, No. 24, Jun. 12, 1978, p. 424, column 1, No. 177021a; Columbus, Ohio, U.S.A. & JP-A 77 122 638 (Unilever N.V.), 10-15-77.
Patent Abstracts of Japan, vol. 4, No. 124, (C-23), Sep. 2, 1980, p. 6C23; Tokyo, Japan & JP-A 55 76810 (Kao Sekken).

*Primary Examiner*—P. E. Willis, Jr.
*Attorney, Agent, or Firm*—Oblon, Fisher, Spivak, McClelland & Maier

[57] ABSTRACT

A creamy cleansing composition comprises the following four components: (A) one or more phosphoric ester surfactants, (B) an organic or inorganic salt, (C) polyethylene glycol and (D) an ethylene oxide addition type non-ionic surface active agent or a cationic surface active agent. The cleansing composition is gentle to the skin or hair, and stable without separation for a long period of time.

7 Claims, No Drawings

CREAMY CLEANSING COMPOSITIONS

BACKGROUND OF THE INVENTION

1. Field of the Invention

The present invention relates to a creamy cleansing composition, and particularly to a creamy cleansing composition which comprises a phosphoric ester surfactant, an organic or inorganic salt, a polyethylene glycol and a cationic surface active agent and which is mild to the skin and hair and stable for a long period of time.

2. Description of the Prior Art

Creamy cleansing compositions are favourably used, as they are not only convenient in handling, but also they have good solubility in water and present superior appearance. The conventional creamy cleansing compositions are composed mainly of an anionic surface active agent such as a salt of a higher fatty acid or a sulfuric ester of a higher alcohol, and, dispersed therein, a substance of a high melting point, such as a pearling agent, a higher fatty acid or wax, and they are not completely satisfactory in their mildness as they give irritation to the skin.

Recently, it has been proposed to use a phosphoric ester surfactant, which is a kind of anionic surface active agents, for a cleansing composition, as it is an extremely mild surface active agent which gives little irritation to the skin. However, if this phosphoric ester surfactant is incorporated alone with the above mentioned other components, the resulting creamy cleansing composition tends to have an inferior cleansing power and less stability and it is likely to undergo separation in a relatively short period of time.

SUMMARY OF THE INVENTION

Accordingly, the present inventors have conducted extensive researches to obtain a creamy cleansing composition which maintains excellent mildness and superior cleansing power of the phosphoric ester surfactant and which is stable for a long period of time, and have found that it is possible to obtain a stable creamy cleansing composition, which undergoes little change in its viscosity irrespective of the temperature, without impairing the desirable characteristics which the phosphoric ester surfactant inherently possesses, by combining the phosphoric ester surfactant with an organic or inorganic salt, polyethylene glycol and an ethylene oxide addition type non-ionic or cationic surface active agent and using the combined material as the major constituent of the creamy cleansing composition.

Thus, the present invention provides a creamy cleansing composition comprising the following four components:

(A) from 10 to 60% by weight of one or more phosphoric ester surfactants represented by the general formulas (I) or (II),

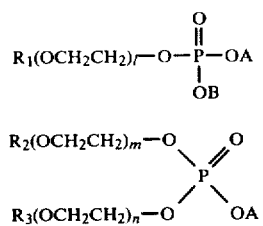

where each of $R_1$, $R_2$ and $R_3$ represents a saturated or unsaturated hydrocarbon group having from 8 to 18 carbon atoms, each A and B represents a hydrogen atom, an alkali metal, ammonium or an alkanolamine having 2 or 3 carbon atoms, and each of l, m, and n is 0 or an integer of from 1 to 10, (B) from 0.5 to 15% by weight of an organic or inorganic salt, (C) from 0.5 to 15% by weight of polyethylene glycol having a molecular weight of from 4,000 to 10,000, and (D) a surface active agent selected from the group consisting of (1) from 0.1 to 15% by weight of an ethylene oxide (at least 50 moles) addition type non-ionic surface active agent, (2) from 0.05 to 10% by weight of a cationic surface active agent represented by the general formula (III),

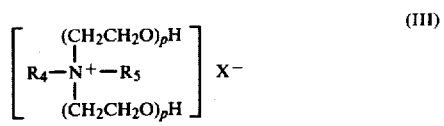

where $R_4$ represents a saturated or unsaturated hydrocarbon group having from 8 to 18 carbon atoms, $R_5$ represents a methyl group or an ethyl group, X represents a halogen atom, and each of p and q represents an integer of from 1 to 15, and (3) from 0.05 to 10% by weight of a cationic surface active agent represented by the general formula (IV),

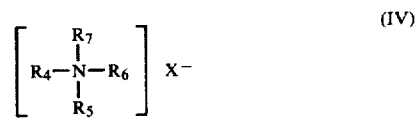

where $R_6$ represents a methyl group or an ethyl group, $R_7$ represents a saturated or unsaturated hydrocarbon group having from 8 to 18 carbon atoms, and $R_4$, $R_5$ and X have the same meanings as defined above.

DETAILED DESCRIPTION OF THE INVENTION

The phosphoric ester surfactants as the component (A) of the present invention, may be used alone or in combination as a mixture of the compounds represented by the formulas (I) and (II) in an optional ratio. Preferred is a mixture of the compounds of the formula (I) and the compounds of the formula (II) in a weight ratio of from 100:0 to 50:50. Further, the compounds of the formulas (I) and (II) wherein l, m or n is 0, are preferred. Particularly preferred are, for instance, sodium mono- or di-laurly phosphate, potassium mono- or di-laurylphosphate, diethanolamine mono- or di-lauryl phosphate, triethanolamine mono- or di-laurylphosphate, sodium mono- or di-myristylphosphate, potassium mono- or di-myristylphosphate, triethanolamine mono- or dimyristylphosphate, sodium mono- or di-oleylphosphate, potassium mono- or di-oleylphosphate, potassium mono-palmitylphosphate, triethanolamine mono-palmitylphosphate, potassium mono-stearylphosphate, and triethanolamine mono-stearylphosphate.

The phosphoric ester surfactants of the component (A) are incorporated in the creamy cleansing compositions in an amount of from 10 to 60% by weight (hereinafter referred to simply as %), preferably from 25 to 45%.

As the organic or inorganic salt as the component (B) of the present invention, there may be mentioned a salt of, for instance, an organic acid such as a carboxylic or hydroxycarboxylic acid e.g. citric acid, oxalic acid, malic acid, succinic acid, lactic acid, or tartaric acid, or an inorganic acid such as hydrochloric acid, hydrobromic acid, nitric acid, sulfuric acid, carbonic acid, phosphoric acid, or thiocyanic acid. As the cation which forms the salts, there may be mentioned an alkali metal such as sodium, potassium, or lithium; an alkaline earth metal such as calcium, or magnesium; or aluminum or ammonium. As the component (B), inorganic salts are superior, in effectiveness, to organic salts. Particularly suitable are alkali metal salts or ammonium salts. Preferred salts are, for instance, sodium chloride, potassium chloride, lithium chloride, sodium bromide, ammonium chloride, sodium nitrate, sodium sulfate, sodium carbonate, sodium monohydrogenphosphate, sodium dihydrogenphosphate, and sodium thiocyanate.

The organic or inorganic salts of the component (B) are incorporated alone or in combination of two or more, in the creamy cleansing compositions in an amount of from 0.5 to 15%, preferably from 3 to 12%.

The polyethylene glycol having a molecular weight of from 4,000 to 10,000, as the component (C) of the present invention, is incorporated in the creamy cleansing composition in an amount of from 0.5 to 15%, preferably from 2 to 13%.

As the ethylene oxide addition type non-ionic surface active agents which are used as the component (D) of the present invention, there may be mentioned adducts which contain at least 50 moles, in an average, of addition-polymerized ethylene oxide. Preferred are, for instance, the following:

(a) a polyoxyethylene (from 80 to 200) alkyl or alkenyl ether, where the number in the parentheses represents an average of moles of addition-polymerized ethylene oxide, and the alkyl group or the alkenyl group has, in an average, from 8 to 20 carbon atoms, (b) a polyoxyethylene (from 80 to 200) mono- or di-higher saturated or unsaturated fatty acid ester, where the number in the parentheses has the same meaning as defined above, and the fatty acid has, in an average, from 8 to 20 carbon atoms, (c) a polyoxyethylene (from 60 to 150) castor oil or hydrogenated castor oil, where the number in the parentheses has the same meaning as defined above, and (d) a polyoxyethylene (from 50 to 100) mono- or di-higher saturated or unsaturated fatty acid sorbitan ester, where the number in the parentheses has the same meaning as defined above and the fatty acid has, in an average, from 8 to 20 carbon atoms.

Further, the cationic surface active agents represented by the above general formulas (III) and (IV), which are used as the component (D) of the present invention, may be used alone or in combination as a mixture of two or more. Preferred compounds of the formula (III) are, for instance, myristyl dipolyoxyethylene methylammonium chloride or bromide ($p+q=6$ to 20), myristyl dipolyoxyethylene ethylammonium chloride or bromide ($p+q=6$ to 20), palmityl dipolyoxyethylene methylammonium chloride or bromide ($p+q=6$ to 20), palmityl dipolyoxyethylene ethylammonium chloride or bromide ($p+q=6$ to 20) and stearyl dipolyoxyethylene methylammonium chloride or bromide ($p+q=6$ to 20). Preferred compounds of the formula (IV) are, for instance, dilauryl dimethylammonium chloride or bromide, dimyristyl dimethylammonium chloride or bromide, dipalmityl dimethylammonium chloride or bromide, and distearyl dimethylammonium chloride or bromide. Particularly preferred among these cationic surface active agents, are ethylene oxide addition dialkyl type cationic surface active agents.

The surface active agents of the component (D) are incorporated in the creamy cleansing composition in an amount of from 0.1 to 15%, preferably from 1 to 12%, in the case of the ethylene oxide addition type non-ionic surface active agents, and in an amount of from 0.05 to 10%, preferably from 0.2 to 7%, in the case of the cationic surface active agents.

The production of the creamy cleansing composition of the present invention is not restricted to any special process, and the composition may readily be prepared according to usual processes. For example, the following method may be mentioned as a preferred process. Namely, the phosphoric ester surfactant is mixed with water, and heated and stirred to form a homogeneous mixture. The mixture is then heated to a temperature of from 60° to 80° C., and added thereto are polyethylene glycol and the ethylene oxide addition type non-ionic surface active agent. After stirring for a while, the mixture is gradually cooled, while stirring, down to room temperature, whereupon the creamy cleansing composition is obtained. The whole operation should preferably be carried out under a reduced pressure so as to prevent formation of foams.

Further, the pH of the creamy cleansing compositions of the present invention, should most preferably be within a range of from 6 to 8 in view of their foaming and irritative characteristics.

Further, it is possible to incorporate into the creamy cleansing compositions of the invention, such additives as colouring substances, perfumes, bacteriocides, antiphologistics, chelating agents, viscosity regulating agents, foaming agents, antiseptics, wetting agents, and other kinds of surface active agents, as the case requires.

Thus prepared creamy cleansing compositions are gentle to the skin and hair and stable for a long period of time.

Now, the invention will be described in further detail with reference to Examples. However, it should be understood that the present invention is not limited by these Examples.

EXAMPLE 1

Creamy cleansing compositions (pH 7.0) having such compositions as shown in Tables 1-A and 1-B were prepared and left to stand for 60 days. Then, the separation stability of the pastes was investigated. The results obtained are shown in Tables 2-A and 2-B.

TABLE 1-A

| Creamy cleansing compostions | | Sodium monolauryl-phosphate | Sodium dilauryl-phosphate | Sodium chloride | Polyethylene glycol (Molecular weight: 6,000) | Polyoxyethylene (100) monopalmitate | Water |
|---|---|---|---|---|---|---|---|
| Products of the present invention | 1 | 28(%) | 9(%) | 6(%) | 5(%) | 2(%) | Balance |
| | 2 | 28 | 9 | 8 | 4 | 2 | Balance |
| | 3 | 28 | 9 | 10 | 4 | 1 | Balance |
| | 4 | 28 | 9 | 8 | 2 | 4 | Balance |
| Comparative products | 5 | 28 | 9 | 0 | 5 | 2 | Balance |
| | 6 | 28 | 9 | 0 | 8 | 5 | Balance |
| | 7 | 28 | 9 | 6 | 0 | 2 | Balance |
| | 8 | 28 | 9 | 6 | 0 | 7 | Balance |
| | 9 | 28 | 9 | 6 | 5 | 0 | Balance |
| | 10 | 28 | 9 | 6 | 7 | 0 | Balance |

TABLE 1-B

| Creamy cleansing compositions | | Sodium monolauryl-phosphate (% by weight) | Sodium dilauryl-phosphate (% by weight) | Sodium chloride (% by weight) | Polyethylene glycol (Molecular weight: 6,000 (% by weight) | Palmityl dipolyoxyethylene methyl-ammonium chloride (p + q = 10) (% by weight) | Water |
|---|---|---|---|---|---|---|---|
| Products of the present invention | 11 | 28 | 9 | 4 | 7 | 3 | balance |
| | 12 | 28 | 9 | 6 | 6 | 2 | balance |
| | 13 | 28 | 9 | 8 | 4 | 2 | balance |
| | 14 | 28 | 9 | 10 | 4 | 1 | balance |
| Comparative products | 15 | 28 | 9 | 0 | 7 | 3 | balance |
| | 16 | 28 | 9 | 0 | 9 | 5 | balance |
| | 17 | 28 | 9 | 7 | 0 | 3 | balance |
| | 18 | 28 | 9 | 7 | 0 | 7 | balance |
| | 19 | 28 | 9 | 7 | 4 | 0 | balance |
| | 20 | 28 | 9 | 7 | 7 | 0 | balance |

TABLE 2-A

| | | Separation stability (after being left to stand for 60 days) | | |
|---|---|---|---|---|
| | | 5° C. | 25° C. | 40° C. |
| Products of the present invention | 1 | o | o | o |
| | 2 | o | o | o |
| | 3 | o | o | o |
| | 4 | o | o | o |
| Comparative products | 5 | x | x | x |
| | 6 | x | x | x |
| | 7 | x | x | x |
| | 8 | x | x | x |
| | 9 | x | x | x |
| | 10 | x | x | x |

TABLE 2-B

| | | Separation stability of pastes | | |
|---|---|---|---|---|
| | | 5° C. | 20° C. | 40° C. |
| Products of the present invention | 11 | o | o | o |
| | 12 | o | o | o |
| | 13 | o | o | o |
| | 14 | o | o | o |
| Comparative products | 15 | x | x | x |
| | 16 | x | x | x |
| | 17 | x | x | x |
| | 18 | x | x | x |
| | 19 | o | x | x |
| | 20 | o | x | x |

Evaluation standards for the separation stability:
o: No change is observed in the state of the paste.
x: Separated liquid is observed.

It is apparent from the results shown in Table 2 that in case any one of the components (A) to (D) of the present invention is lacking the composition lacks in stability and no satisfactory creamy cleansing composition is obtainable.

EXAMPLE 2

With respect to the creamy cleansing compositions listed in Table 1-A of Example 1, the hardness of the respective pastes was measured. The results obtained are shown in Table 3.

TABLE 3

| Creamy cleansing compositions | | Hardness of pastes (ranking) | | |
|---|---|---|---|---|
| | | 5° C. | 20° C. | 40° C. |
| Products of the present invention | 1 | D | C | B |
| | 2 | D | C | B |
| | 3 | D | C | B |
| | 4 | D | C | B |
| Comparative products | 5 | — | — | — |
| | 6 | — | — | — |
| | 7 | — | — | — |
| | 8 | — | — | — |
| | 9 | E | — | — |
| | 10 | E | — | — |

Evaluation standards for the hardness of the pastes:
With use of a penetrometer, penetration of the needle into the paste (mm) was measured after the loading period of time of 5 seconds and the standards for the hardness were determined and ranked as follows:

TABLE 4

| Ranking | Degree of the hardness | Penetration of the needle P (mm) |
|---|---|---|
| A | soft | 10 < P |
| B | Slightly soft | 8 < P ≦ 10 |
| C | Appropriate | 4 < P ≦ 8 |

TABLE 4-continued

| Ranking | Degree of the hardness | Penetration of the needle P (mm) |
|---|---|---|
| D | Slightly hard | 2 < P ≦ 4 |
| E | Hard | 0 ≦ P ≦ 2 |

(Note) In the ranking, B to D indicate that when the paste is filled in a tube, it presents no practical problem in the sqeezability and shape maintaining property. A indicates that the paste is too soft to maintain its shape. E indicates that the paste is too hard to squeeze out thuspresenting a practical problem.

EXAMPLE 3

The stability and hardness of the pastes due to changes in the molecular weight and the amounts of the polyethylene glycol, were investigated with use of the following creamy cleansing compositions (a) and (b). The results obtained are shown in Table 7. Creamy cleansing composition (a):

| | |
|---|---|
| Sodium monolaurylphosphate | 28% |
| Sodium dilaurylphosphate | 9 |
| Sodium sulfate | 6 |
| Polyethylene glycol | (see Table 5) |
| Polyoxyethylene (140) monostearate | 2 |
| Sorbitol | 6 |
| Perfume | 0.3 |
| Water | Balance |
| (pH 7.0) | |

TABLE 5

| Creamy cleansing compositions | Molecular weights of polyethylene glycol | Amounts of polyethylene glycol (%) |
|---|---|---|
| a-1 | 1,000 | 10 |
| a-2 | 2,000 | 10 |
| a-3 | 4,000 | 10 |
| a-4 | | 0.4 |
| a-5 | | 1 |
| a-6 | | 3 |
| a-7 | 6,000 | 10 |
| a-8 | | 15 |
| a-9 | | 20 |
| a-10 | 10,000 | 10 |
| a-11 | 15,000 | 10 |

Creamy cleansing composition (b):

| | | |
|---|---|---|
| Sodium monolaurylphosphate | 30 | (% by weight) |
| Sodium dilaurylphosphate | 7 | |
| Sodium chloride | 8 | |
| Polyethylene glycol | (see Table 6) | |
| Stearyl dipolyoxyethylene methylammonium, chloride (p + q = 14) | 2 | |
| Glycerin | 6 | |
| Perfume | 0.2 | |
| Water | Balance | |
| (pH 7.0) | | |

TABLE 6

| Creamy cleaning compositions | Molecular weights of polyethylene glycol | Amounts of polyethylene glycol (% by weight) |
|---|---|---|
| b-1 | 1,000 | 10 |
| b-2 | 2,000 | 10 |
| b-3 | 4,000 | 10 |
| b-4 | | 0.4 |
| b-5 | | 1 |
| b-6 | | 3 |
| b-7 | 6,000 | 10 |
| b-8 | | 15 |
| b-9 | | 20 |
| b-10 | 10,000 | 10 |
| b-11 | 15,000 | 10 |

TABLE 7

| Creamy cleansing compositions Nos. | Separation Stability of pastes* | Hardness of pastes** (ranking) |
|---|---|---|
| a-1 | x | — |
| a-2 | x | — |
| a-3 | o | B |
| a-4 | x | — |
| a-5 | o | B |
| a-6 | o | C |
| a-7 | o | C |
| a-8 | o | D |
| a-9 | o | E |
| a-10 | o | D |
| a-11 | o | E |
| b-1 | x | — |
| b-2 | x | — |
| b-3 | o | B |
| b-4 | x | — |
| b-5 | o | B |
| b-6 | o | C |
| b-7 | o | C |
| b-8 | o | D |
| b-9 | o | E |
| b-10 | o | D |
| b-11 | o | E |

*The separation stability of the pastes was determined in accordance with the standards of Example 1, with respect to the state after being left to stand for 60 days at 40° C.
**The hardness of the pastes was determined in accordance with the standards of Example 2.

EXAMPLE 4

The effect of various inorganic salts on the creamy cleansing compositions, is shown in Table 8.
Creamy cleansing composition (c):

| | |
|---|---|
| Sodium monolaurylphosphate | 28% |
| Sodium monomyristylphosphate | 10 |
| Sodium mono-oleylphosphate | 4 |
| Inorganic salt | (see Table 8) |
| polyethylene glycol (Molecular weight: 8,000) | 7 |
| polyoxyethylene (160) dipalmitate | 5 |
| Glycerin | 10 |
| Perfume | 0.3 |
| Water | Balance |
| (pH 7.5) | |

Creamy cleansing composition (d):

| | | |
|---|---|---|
| Sodium monolaurylphosphate | 28 | (% by weight) |
| Sodium monomyristylphosphate | 10 | |
| Sodium mono-oleylphosphate | 4 | |
| Salt | (see Table 8) | |
| Polyethylene glycol (Molecular weight: 8,000) | 7 | |
| Myristyl dipolyoxyethylene methylammonium chloride (P + q = 10) | 3 | |
| Dipalmityl dimethylammonium chloride | 0.5 | |
| Glycerin | 1.0 | |
| Perfume | 0.3 | |
| Water | Balance | |
| (pH 7.9) | | |

TABLE 8

| Salts | Creamy cleansing composition (c) | | | Creamy cleansing composition (d) | | |
|---|---|---|---|---|---|---|
| | Amounts (% by weight) | Separation stability of pastes | Hardness of pastes (ranking) | Amounts (% by weight) | Separation stability of pastes | Hardness of pastes (ranking) |
| Potassium chloride | 5 | o | C | 6 | o | C |
| Lithium chloride | 5 | o | C | 6 | o | C |
| Sodium bromide | 5 | o | C | 6 | o | C |
| Ammonium chloride | 5 | o | C | 6 | o | C |
| Sodium nitrate | 5 | o | C | 6 | o | C |
| Sodium sulfate | 5 | o | C | 6 | o | C |
| Sodium carbonate | 5 | o | C | 6 | o | C |
| Disodium hydrogenphosphate | 5 | o | C | 6 | o | C |
| Sodium dihydrogenphosphate | 5 | o | C | 6 | o | C |
| Sodium thiocyanate | 5 | o | C | 6 | o | C |
| Sodium citrate | 5 | o | B | 6 | o | C |
| Sodium chloride | 0.3 | x | A | 0.3 | x | A |
| Sodium chloride | 0.7 | o | B | 0.7 | o | B |
| Sodium chloride | 15 | o | D | 15 | o | D |
| Sodium chloride | 20 | o | E | 20 | o | E |

(Note) The separation stability of the pastes was determined with respect to the state after being left to stand for 60 days at 40° C., and the hardness of the pastes was determined with respect to the state after being left to stand for 60 days at 20° C., in accordance with the standards indicated in Example 2.

EXAMPLE 5

The effect of various cationic surface active agents on the creamy cleansing compositions, is shown in Table 9.
Creamy cleansing composition:

| | | |
|---|---|---|
| Sodium monolaurylphosphate | 28 | (% by weight) |
| Sodium dilaurylphosphate | 5 | |
| Sodium polyoxyethylene (3) monolauryl phosphate | 5 | |
| Sodium sulfate | 8 | |
| Polyethylene glycol (Molecular weight: 6,000) | 6 | |
| Cationic surface active agent | (see Table 9) | |
| Sorbitol | 10 | |
| Perfume | 0.2 | |
| Water | Balance | |
| (pH 6.5) | | |

EXAMPLE 6

The effect of various non-ionic surface active agents on the creamy cleansing compositions, is shown in Table 10.
Creamy cleansing composition:

| | |
|---|---|
| Sodium monolaurylphosphate | 40 (%) |
| Sodium chloride | 7 |
| Polyethylene glycol (Molecular weight: 6000) | 4 |
| Non-ionic surface active agent | (see Table 10) |
| Sorbitol | 6 |
| Water | Balance |
| (pH 6.7) | |

(Note) The separation stability of the pastes was determined with respect to the state after being left to stand for 60 days at 40° C., and the hardness of the pastes was determined with respect to the state after being left to stand for 60 days at 20° C., in accordance with the standards identified in Example 2.

TABLE 9

| | Cationic surface active agents | Amounts (% by weight) | Separation stability of pastes | Hardness of pastes (ranking) |
|---|---|---|---|---|
| Products of the present invention | Palmityl dipolyoxyethylene Methylammonium chloride (p + q = 16) | 0.04 | x | — |
| | Palmityl dipolyoxyethylene Methylammonium chloride (p + q = 16) | 0.2 | o | B |
| | Palmityl dipolyoxyethylene Methyl ammonium chloride (p + q = 16) | 2 | o | C |
| | Palymityl dipolyoxyethylene Methylammonium chloride (p + q = 16) | 5 | o | C |
| | Palymityl dipolyoxyethylene Methylammonium chloride (p + q = 16) | 12 | o | E |
| | Lauryl dipolyoxyethylene methylammonium bromide (p + q = 20) | 2 | o | C |
| | Myristyl dipolyoxyethylene methylammonium chloride (p + q = 6) | 2 | o | C |
| | Stearyl dipolyoxyethylene methylammonium chloride (p + q = 10) | 2 | o | C |
| | Palmityl dipolyoxyethylene ethylammonium bromide (p + q = 8) | 2 | o | C |
| | Dilauryl dimethylammonium chloride | 2 | o | C |
| | Distearyl dimethylammonium chloride | 2 | o | C |
| | Dimyristyl dimethylammonium bromide | 2 | o | C |
| Comparative products | Stearyl trimethylammonium chloride | 2 | x | — |
| | Palmityl trimethylammonium bromide | 2 | x | — |
| | Benzyl lauryl methyl ammonium chloride | 2 | x | — |

TABLE 10

| Non-ionic surface active agents | Amounts (%) | Separation stability of pastes* | Hardness of pastes |
|---|---|---|---|
| $C_{12}H_{25}O(C_2H_4O)_6H$ | 5 | x | — |
| $C_{18}H_{37}O(C_2H_4O)_{40}H$ | 5 | x | — |
| $C_{15}H_{31}COO(C_2H_4O)_{10}H$ | 5 | x | — |
| $C_{15}H_{31}COO(C_2H_4O)_{30}H$ | 5 | x | — |
| $C_{17}H_{35}COO(C_2H_4O)_{40}H$ | 5 | x | — |
| Polyoxyethylene (20) hydrogenated castor oil | 5 | x | — |
| Polyoxyethylene (20) monopalmitic acid sorbitan ester | 5 | x | — |
| Monostearic acid sorbitan ester | 5 | x | — |
| Distearic acid sorbitan ester | 5 | x | — |
| Polyoxyethylene (80) dilauric acid sorbitan ester | 5 | o | C |
| Polyoxyethylene (80) hydrogenated castor oil | 5 | o | C |
| Polyoxyethylene (80) monostearic acid sorbitan ester | 5 | o | C |
| $C_{18}H_{37}O(C_2H_4O)_{120}H$ | 5 | o | C |
| Polyoxyethylene (50) monopalmitic acid sorbitan ester | 5 | o | C |
| Polyoxyethylene (50) monopalmitic acid sorbitan ester | 20 | o | E |

*After being left to stand for 60 days at 40° C.

EXAMPLE 7

Creamy cleansing compositions having the following compositions, were prepared.

| | |
|---|---|
| (i) Sodium monolaurylphosphate | 27 (%) |
| Potassium monomyristylphosphate | 5 |
| Potassium dimyristylphosphate | 2 |
| Sodium polyoxyethylene (3) monolaurylether phosphate | 5 |
| Sodium sulfate | 4 |
| Polyoxyethylene glycol (Molecular weight: 4,000) | 8 |
| Polyoxyethylene (140) distearate | 3 |
| Glycerin | 7 |
| Perfume, colouring agent, and antiseptics | Appropriate amounts |
| Water | Balance |
| (pH 7.6) | |
| (ii) Potassium polyoxyethylene (4) myristylether phosphate (mono/di = 2/1) | 45 |
| MIRANOL C2M (Amphoteric surface active agent made by MIRANOL CO.) | 5 |
| Magnesium chloride | 4 |
| Sodium chloride | 8 |
| Polyethylene glycol (Molecular weight: 8,000) | 4 |
| Polyoxyethylene (100) monostearate | 3 |
| Glycerin | 10 |
| Perfume and antiseptic | Appropriate amounts |
| Water | Balance |
| (pH 6.9) | |
| (iii) Sodium monolaurylphosphate | 35 |
| Triethanolamine polyoxyethylene (4) laurylether phosphate (mono/di = 3/1) | 10 |
| CARBOPOL 941 (Carboxy vinyl polymer made by Goodrich Co.) | 1 |
| Sodium carbonate | 8 |
| Polyethylene glycol (Molecular weight: 10,000) | 5 |
| Polyoxyethylene (80) hydrogenated castor oil | 5 |
| Propylene glycol | 10 |
| Perfume and antiseptic | Appropriate amounts |
| Water | Balance |
| (pH 7.2) | |
| (iv) Sodium monolaurylphosphate | 27 (% by weight) |
| Potassium monomyristylphosphate | 5 |
| Potassium dimyristylphosphate | 2 |
| Sodium polyoxyethylene (5) monolauryl ether phosphate | 5 |
| Sodium sulfate | 5 |
| Polyethylene glycol (Molecular weight: 4,000) | 7 |
| Stearyl dipolyoxyethylene methylammonium chloride (p + q = 10) | 1 |
| Dilauryl dimethylammonium bromide | 0.5 |
| Glycerin | 8 |
| Perfume, colouring agent and antiseptic | Appropriate amounts |
| Water | Balance |
| (pH = 7.3) | |
| (v) Lithium polyoxyethylene (4) myristylether phosphate (mono/di = 3/1) | 2 (% by weight) |
| Lithium monolaurylphosphate | 5 |
| Sodium monolaurylphosphate | |
| Sodium chloride | 5 |
| Polyethylene glycol (Molecular weight: 8,000) | 6 |
| Lauryl dipolyoxyethyllene methylammonium chloride (p + q 8) | 1 |
| Silicic acid anhydride | 0.5 |
| Polyoxyethylene (100) dipalmitic | 0.5 |
| Sorbitol | 8 |
| Perfume, colouring agent and antiseptic | Appropriate amounts |
| Water | Balance |
| (pH 7.0) | |
| (vi) Sodium monolaurylphosphate | 40 (% by weight) |
| Magnesium chloride | 2 |
| Lithium chloride | 3 |
| MIRANOL C2M (Amphoteric surface active agent made by MIRANOL CO.) | 2 |
| Polyethylene glycol (Molecular weight: 6,000) | 6 |
| Dimyristyl dimethylammonium chloride | 3 |
| Propylene glycol | 8 |
| CARBOPOL 941 (Carboxy vinyl polymer made by Goodrich Co.) | 0.5 |
| Polyoxyethylene (100) monostearate | 2 |
| Perfume, colouring agent and antiseptic | Appropriate Amounts |
| Water | Balance |
| (pH 7.6) | |

Each of the creamy cleansing compositions thus prepared, was gentle to the skin and was stable without separation during storage for a long period of time.

What is claimed is:

1. A creamy cleansing composition comprising components:

(a) from 10 to 60% by weight of one or more phosphoric ester surfactants represented by the general formulas (I) or (II).

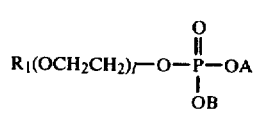

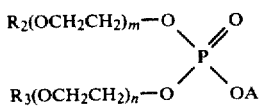

where each of $R_1$, $R_2$ and $R_3$ represents a saturated or unsaturated hydrocarbon group having from 8 to 18 carbon atoms, each of A and B represents a hydrogen atom, an alkali metal, ammonium or an alkanolamine having 2 or 3 carbon atoms, and each of l, m and n is 0 or an integer of from 1 to 10;

(b) from 0.5 to 15% by weight of an organic or inorganic salt, selected from the group consisting of an alkali metal, alkali earth metal or ammonium salt of carboxylic acid, hydroxycarboxylic acid, hydrochloric acid, hydrobromic acid, nitric acid, sulfuric acid, carbonic acid, phosphoric acid and thiocyanic acid;

(c) from 0.5 to 15% by weight of polyethylene glycol having a molecular weight of from 4,000 to 10,000; and (d) a surface active agent selected from the group consisting of (1) from 0.1 to 15% by weight of an ethylene oxide (at least 50 moles) addition type non-ionic surface active agent; (2) from 0.05 to 10% by weight of a cationic surface active agent represented by the general formula (III)

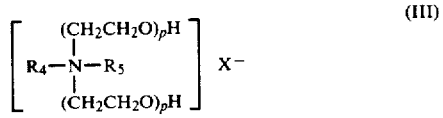

where $R_4$ represents a saturated or unsaturated hydrocarbon group having from 8 to 18 carbon atoms, $R_5$ represents a methyl group or an ethyl group, X represents a halogen atom, and each of p and q represents an integer of from 1 to 15; and (3) from 0.05 to 10% by weight of a cationic surface active agent represented by the general formula (IV),

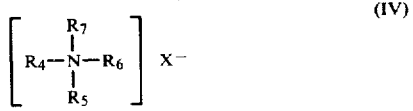

where $R_6$ represents a methyl group or an ethyl group, $R_7$ represents a saturated or unsaturated hydrocarbon group having from 8 to 18 carbon atoms, and $R_4$, $R_5$ and X have the same meanings as defined above.

2. The creamy cleansing composition of claim 1, wherein the component (a) is a phosphoric ester surfactant selected from the group consisting of the compounds of the general formulas (I) and (II) where each of l, m and n is 0.

3. The creamy cleansing composition of claim 1, wherein the component (a) is a mixture of phosphoric ester surfactants composed of compounds of the general formula (I) and compounds of the general formula (II) in a weight ratio of from 100:0 to 50:50.

4. The creamy cleansing composition of claim 1, wherein the inorganic salt is selected from the group consisting of sodium chloride, potassium chloride, lithium chloride, sodium bromide, ammonium chloride, sodium nitrate, sodium sulfate, sodium carbonate, sodium monohydrogenphosphate, sodium dihydrogenphosphate and sodium thiocyanate.

5. The creamy cleansing composition of claim 1, wherein the non-ionic surface active agent of the component (d) is selected from the group consisting of:

(i) a polyoxyethylene (from 80 to 200) alkyl or alkenyl ether, where the number in the parenthesis represents an average of moles of addition-polymerized ethylene oxide, and the alkyl group or the alkenyl group has, in an average, from 8 to 20 carbon atoms, (ii) a polyoxyethylene (from 80 to 200) mono- or di-higher saturated or unsaturated fatty acid ester, where the number in the parenthesis has the same meaning as defined above, and the fatty acid has, in an average, from 8 to 20 carbon atoms, (iii) a polyoxyethylene (from 60 to 150) castor oil or hydrogenated castor oil, where the number in the parenthesis has the same meaning as defined above, and (iv) a polyoxyethylene (from 50 to 100) mono- or di-higher saturated or unsaturated fatty acid sorbitan ester, where the number in the parenthesis has the same meaning as defined above and the fatty acid has, in an average, from 8 to 20 carbon atoms.

6. The creamy cleansing composition of claim 1, wherein the cationic surface active agent represented by the general formula (III) as the component (d) is selected from the group consisting of myristyl dipolyoxyethylene methylammonium chloride or bromide (p+q=6 to 20), a myristyl dipolyoxyethylene ethylammonium chloride or bromide (p+q=6 to 20), a palmityl dipolyoxyethylene methylammonium chloride or bromide (p+q=6 to 20), a palmityl dipolyoxyethylene ethylammonium chloride or bromide (p+q=6 to 20) and a stearyl dipolyoxyethylene methylammonium chloride or bromide (p+q=6 to 20).

7. The creamy cleansing composition of claim 1, wherein the cationic surface active agent represented by the general formula (IV) as the component (d) is selected from the group consisting of dilauryl dimethylammonium chloride or bromide, dimyristyl dimethylammonium chloride or bromide, dipalmityl dimethylammonium chloride or bromide and distearyl dimethylammonium chloride or bromide.

* * * * *